United States Patent
Gulani et al.

(10) Patent No.: US 10,898,089 B2
(45) Date of Patent: Jan. 26, 2021

(54) MAGNETIC RESONANCE FINGERPRINTING (MRF) WITH EFFICIENT ACQUISITION SCHEMES

(71) Applicant: Case Western Reserve University, Cleveland, OH (US)

(72) Inventors: Vikas Gulani, Cleveland Heights, OH (US); Mark Griswold, Shaker Heights, OH (US); Dan Ma, Cleveland, OH (US); Alice Yang, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 1083 days.

(21) Appl. No.: 14/690,511

(22) Filed: Apr. 20, 2015

(65) Prior Publication Data

US 2015/0301147 A1   Oct. 22, 2015

Related U.S. Application Data

(60) Provisional application No. 61/982,588, filed on Apr. 22, 2014.

(51) Int. Cl.
  *G01R 33/44* (2006.01)
  *A61B 5/026* (2006.01)
  (Continued)

(52) U.S. Cl.
  CPC ............ *A61B 5/0263* (2013.01); *A61B 5/055* (2013.01); *A61B 5/4064* (2013.01);
  (Continued)

(58) Field of Classification Search
  CPC ..... A61B 5/0263; A61B 5/055; A61B 5/4064; A61B 1/00; A61B 17/00; A61B 2217/00;
  (Continued)

(56) References Cited

U.S. PATENT DOCUMENTS 8,723,518 B2 * 5/2014 Seiberlich ............ G01R 33/543
                                                          324/307
9,097,781 B2 * 8/2015 Griswold ........... G01R 33/5612
(Continued)

FOREIGN PATENT DOCUMENTS

| CN | 103654779 | 3/2016 |
| DE | 102014223388 | 5/2016 |
| WO | 2018065618 | 4/2018 |

OTHER PUBLICATIONS

Garner, B.A., A Dictionary of Modern Legal Usage 624 (2d. Ed. 1995).

(Continued)

*Primary Examiner* — Dixomara Vargas
*Assistant Examiner* — Courtney G McDonnough
(74) *Attorney, Agent, or Firm* — Quarles & Brady LLP

(57) ABSTRACT

Example apparatus and methods improve magnetic resonance fingerprinting (MRF) by performing MRF with optimized spatial encoding, parallel imaging, and utilization of field inhomogeneities. Multi-echo radial trajectories and spiral trajectories may acquire data according to sampling schemes based on models of charge distribution on a sphere. Non-uniform sampling schemes may account for differences in detector coil performance. Field inhomogeneities provide spatial information that enhances the spatial separation of an MRF signal and facilitates unaliasing pixels. The field inhomogeneity may be manipulated. An MRF pulse sequence may include frequency selective RF pulses that are determined by the field inhomogeneities. Inhomogeneities combined with selective RF pulses result in higher acquisition efficiency.

51 Claims, 9 Drawing Sheets

Random     3D Golden     Repel

(51) Int. Cl.
- *A61B 5/055* (2006.01)
- *A61B 5/00* (2006.01)
- *G01R 33/563* (2006.01)
- *G01R 33/48* (2006.01)
- *G01R 33/565* (2006.01)
- *G01R 33/56* (2006.01)
- *G01R 33/561* (2006.01)
- *A61B 1/00* (2006.01)
- *G01R 1/00* (2006.01)
- *A61B 17/00* (2006.01)
- *G06T 1/00* (2006.01)
- *G01R 33/50* (2006.01)

(52) U.S. Cl.
CPC ....... G01R 33/448 (2013.01); G01R 33/4818 (2013.01); G01R 33/5602 (2013.01); G01R 33/5608 (2013.01); G01R 33/5611 (2013.01); G01R 33/56366 (2013.01); G01R 33/56563 (2013.01); *A61B 1/00* (2013.01); *A61B 5/742* (2013.01); *A61B 17/00* (2013.01); *A61B 2217/00* (2013.01); *A61B 2218/00* (2013.01); *G01R 1/00* (2013.01); *G01R 33/4828* (2013.01); *G01R 33/50* (2013.01); *G06T 1/00* (2013.01); *G06T 2200/00* (2013.01)

(58) Field of Classification Search
CPC .. A61B 2218/00; A61B 5/742; G01R 33/448; G01R 33/4818; G01R 33/5602; G01R 33/5608; G01R 33/5611; G01R 33/56366; G01R 33/56563; G01R 1/00; G01R 33/4828; G01R 33/50; G06T 1/00; G06T 2200/00
USPC .......... 324/300–322; 600/407–435; 382/128–131
See application file for complete search history.

(56) References Cited

U.S. PATENT DOCUMENTS

| | | | | |
|---|---|---|---|---|
| 9,568,579 | B2* | 2/2017 | Jerecic | G01R 33/561 |
| 9,757,047 | B2 | 9/2017 | Chappell | |
| 9,851,425 | B2 | 12/2017 | Lee | |
| 9,869,739 | B2* | 1/2018 | Griswold | G01R 33/3635 |
| 10,136,824 | B2 | 11/2018 | Hernandez-Garcia | |
| 2006/0244447 | A1 | 11/2006 | Michaeli | |
| 2009/0142273 | A1 | 6/2009 | Pagel | |
| 2010/0261993 | A1 | 10/2010 | van der Kouwe | |
| 2011/0199084 | A1 | 8/2011 | Hasan | |
| 2012/0235678 | A1* | 9/2012 | Seiberlich | G01R 33/56 324/307 |
| 2012/0262165 | A1 | 10/2012 | Griswold | |
| 2012/0262166 | A1 | 10/2012 | Griswold | |
| 2012/0280686 | A1 | 11/2012 | White | |
| 2013/0271132 | A1* | 10/2013 | Griswold | G01R 33/5612 324/309 |
| 2014/0084922 | A1 | 3/2014 | Fu | |
| 2014/0167754 | A1* | 6/2014 | Jerecic | G01R 33/561 324/309 |
| 2014/0232399 | A1* | 8/2014 | Griswold | G01R 33/56 324/309 |
| 2014/0266199 | A1* | 9/2014 | Griswold | G01R 33/56 324/309 |
| 2014/0292330 | A1 | 10/2014 | Gulani | |
| 2014/0327440 | A1* | 11/2014 | Nakanishi | A61B 5/055 324/309 |
| 2015/0301138 | A1* | 10/2015 | Griswold | G01R 33/56563 324/309 |
| 2015/0301140 | A1 | 10/2015 | Lee | |
| 2015/0301144 | A1 | 10/2015 | Griswold | |
| 2015/0301147 | A1* | 10/2015 | Gulani | G01R 33/56563 324/309 |
| 2015/0316634 | A1* | 11/2015 | Griswold | G01R 33/5612 324/309 |
| 2016/0282430 | A1 | 9/2016 | Gulani | |
| 2017/0016971 | A1* | 1/2017 | Heismann | A61B 5/055 |
| 2017/0146623 | A1 | 5/2017 | Cohen | |

OTHER PUBLICATIONS

Heid, O., M. Deimling, and W. Huk. "QUEST—a quick echo split nmr imaging technique." Magnetic resonance in medicine 29.2 (1993): 280-283.

Lee, G. R., et al. (2013) Rapid time-resolved magnetic resonance angiography via a multiecho radial trajectory and GraDes reconstruction, Magnetic Resonance in Medicine, 69(2): 346-59.

Ma et al., Magnetic Resonance Fingerprinting, Nature 495, 187-192 (Mar. 14, 2013).

Wright, K. L., et al. "Theoretical framework for MR fingerprinting with ASL: simultaneous quantification of CBF, transit time, and T1." Proc Int Soc Magn Reson Med. vol. 22. 2014.

Wright, K. L., et al. "Estimation of perfusion properties with MR fingerprinting arterial spin labeling." Magnetic resonance imaging 50 (2018): 68-77.

* cited by examiner

MAGNETIC RESONANCE FINGERPRINTING (MRF) WITH EFFICIENT ACQUISITION SCHEMES

CROSS REFERENCE TO RELATED APPLICATIONS

This application claims the benefit of U.S. Provisional Patent Application 61/982,588 filed Apr. 22, 2014.

FEDERAL FUNDING NOTICE

This invention was made with government support under 1R01EB017219 and HL 094557 awarded by the National Institutes of Health. The government has certain rights in the invention.

BACKGROUND

Conventional magnetic resonance imaging (MRI) produces images that may vary between scanners, technologists, or scan settings. Conventional MRI images are interpreted qualitatively, which produces subjective variability in diagnosis. Magnetic resonance fingerprinting (MRF) provides consistent quantitative parameters maps, which eliminates the variability found in conventional qualitative images. Quantitative parameter maps also reduce or eliminate subjectivity in diagnosis. In MRF, unique signal time courses are generated for pixels. The time course evolves based on tissue properties including T1 and T2, T1 being spin-lattice relaxation, and T2 being spin-spin relaxation.

The signal time course can be matched to an entry in a dictionary. The dictionary may be, for example, a collection of time courses calculated using a range of possible tissue property values in light of quantum physics properties that govern the signal evolution. Performing MRF for multiple pixels yields anatomical maps of tissue properties of interest. MRF may be more efficient than other proposed quantitative methods because MRF quantifies multiple parameters in a single MR acquisition.

MRF assumes that different tissues and different spatial locations have different signal evolutions. In MRF, different tissues may be separated by varying user-controllable MR settings including flip angle (FA), repetition time (TR) or acquisition time in, for example, a pseudo-random fashion. Randomized encoding may be used to separate different spatial locations.

MRF employs a series of varied sequence blocks that simultaneously produce different signal evolutions in different resonant species (e.g., tissues) to which radio frequency (RF) energy is applied. MRF sequence blocks may vary widely, either non-linearly, randomly, and/or pseudo-randomly. Since the sequence blocks may vary widely, the resulting signal evolutions may also vary widely. Sequence blocks may vary in a number of parameters including, but not limited to, echo time, flip angle, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, type of gradient applied between a readout portion of a sequence block and an excitation portion of a sequence block, number of gradients applied between a readout portion of a sequence block and an excitation portion of a sequence block, type of gradient applied during a readout portion of a sequence block, number of gradients applied during a readout portion of a sequence block, amount of RF spoiling, or amount of gradient spoiling. In different embodiments two, three, four, or more parameters may vary between sequence blocks. In different embodiments, the number of parameters varied between sequence blocks may itself vary. For example, A1 (sequence block 1) may differ from A2 in five parameters, A2 may differ from A3 in seven parameters, A3 may differ from A4 in two parameters, and so on. One skilled in the art will appreciate that there are a nearly infinite number of series of sequence blocks that can be created by varying this large number of parameters.

The term "resonant species", as used herein, refers to an item (e.g., water, fat, tissue, material) that can be made to resonate using nuclear magnetic resonance (NMR). By way of illustration, when RF energy is applied to a volume that has bone and muscle tissue, then both the bone and muscle tissue will produce an NMR signal. However the "bone signal" and the "muscle signal" will be different and can be distinguished using MRF. The different signals can be collected over a period of time to identify a signal evolution for the volume. Resonant species in the volume can then be characterized by comparing the signal evolution to known evolutions. Characterizing the resonant species may include identifying a material or tissue type, or may include identifying MR parameters associated with the resonant species. The "known" evolutions may be, for example, simulated evolutions or previously acquired evolutions. A large set of known evolutions may be stored in a dictionary.

Characterizing the resonant species can include identifying different properties of a resonant species (e.g., T1, T2, diffusion resonant frequency, diffusion co-efficient, spin density, proton density). Additionally, other properties including, but not limited to, tissue types, materials, and super-position of attributes can be identified. These properties may be identified simultaneously using MRF, which is described in U.S. Pat. No. 8,723,518 "Nuclear Magnetic Resonance (NMR) Fingerprinting" and in *Magnetic Resonance Fingerprinting*, Ma et al., Nature 495, 187-192 (14 Mar. 2013), the contents of both of which are incorporated herein by reference.

DETAILED DESCRIPTION

Example apparatus and methods improve the efficiency and accuracy of MRF. Conventionally, in MRI, field inhomogeneity is undesirable. In MRF, field inhomogeneity may be exploited to improve acquisition time. Example apparatus and methods accelerate acquisition by using encoding methods that incorporate parallel imaging using spatial information that is inherent in MR receiver coils. In one embodiment, a three dimensional (3D) MRF implementation optimizes spatial encoding and uses parallel imaging with frequency specific RF pulses that use existing or intentionally created field inhomogeneities. The acquisitions may be based, at least in part, on a model of charge distribution on a sphere. Inhomogeneities combined with frequency selective RF pulses yield higher acquisition efficiency.

Example apparatus and methods acquire information about an existing or created inhomogeneity in a magnetic field associated with an MRI apparatus that is going to perform MRF. The inhomogeneity may be fixed or may vary. The inhomogeneity may vary up to each acquisition period during an MRF pulse sequence used during the MRF. The inhomogeneity may be controlled to be less than $2\pi$ per voxel. Once information about the inhomogeneity is known, the MRF may proceed with a regularly scheduled trajectory or with a trajectory that is selected based, at least in part, on the information about the inhomogeneity. Similarly, once information about the inhomogeneity is known, then regularly scheduled acquisition periods or flip angles may be employed or acquisition periods or flip angles can be optimized based, at least in part, on the inhomogeneity. Additionally, once information about the inhomogeneity is available, then the frequency or timing of RF pulses applied during the MRF pulse sequence can be selectively manipulated based, at least in part, on the inhomogeneity.

Figure 3:
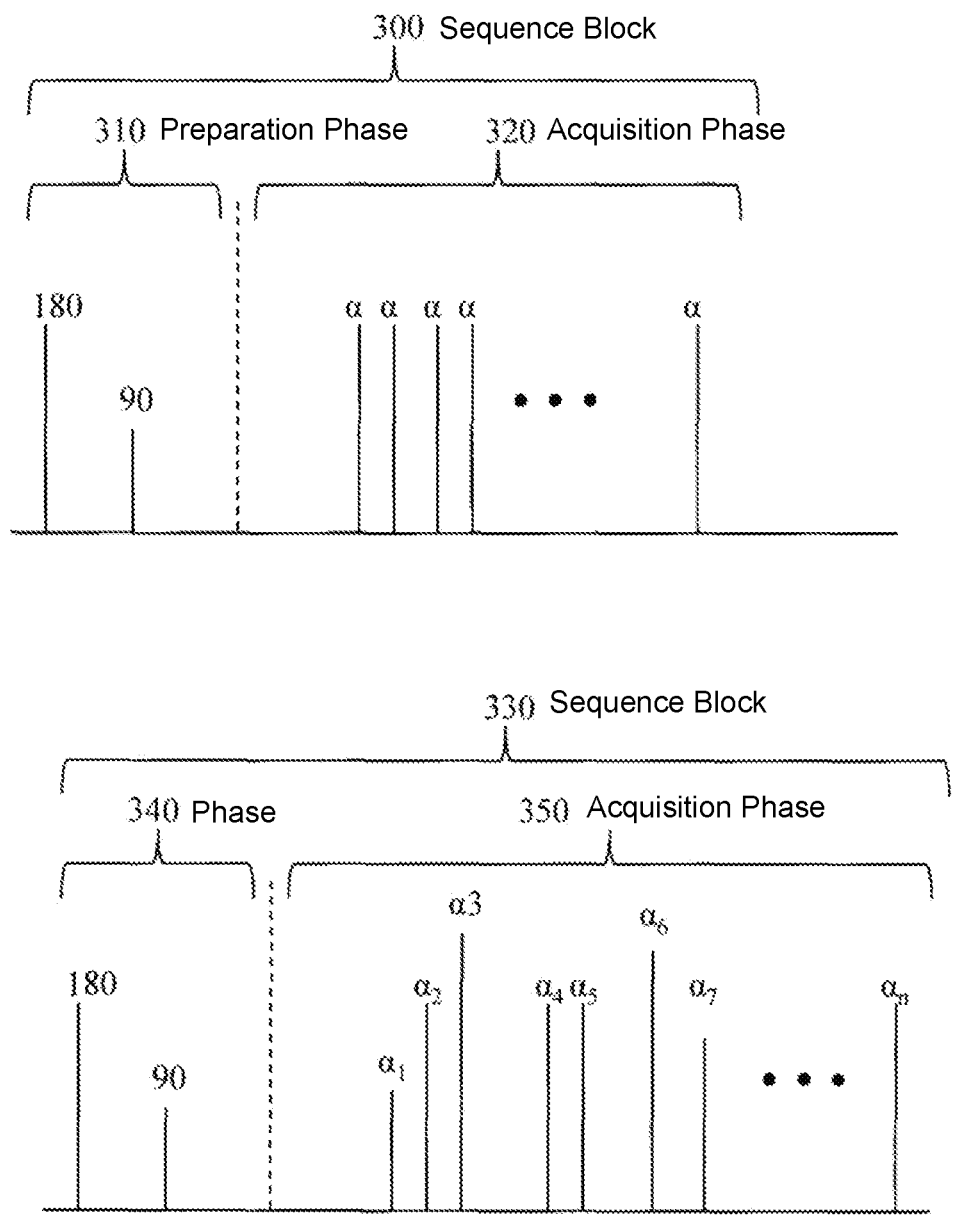
FIG. 3 compares and contrasts conventional sequence blocks to example sequence blocks.

Magnetic resonance (MR) uses pulse sequences. In MRF, the pulse sequences may vary from sequence block to sequence block. FIG. 3 compares and contrasts conventional sequence blocks to example sequence blocks. Sequence block 300 includes a preparation phase 310 and an acquisition phase 320. During acquisition phase 320, multiple acquisitions using the same flip angle and the same interval between acquisitions may be performed. Acquisition phase 320 resembles the Doneva approach, which acquires data from a (k, t) space, where t varies either constantly or linearly. The constant variation facilitates acquiring signal with constant amplitude and phase as required for conventional image reconstruction.

Sequence block 330 also includes a phase 340 and an acquisition phase 350. Notice that acquisition phase 350 is much longer than acquisition phase 320. Unlike acquisition phase 320 where parameters are either fixed or vary linearly, in acquisition phase 350 the parameters may vary widely, either non-linearly, randomly, and/or pseudo-randomly. Parameters that may vary include, but are not limited to, echo time, flip angle, phase encoding, and others. Note also that while phase 340 may, in some examples, be a preparation phase or preparation-like phase, that phase 340 does not necessarily perform a conventional image-centric preparation.

Figure 4:
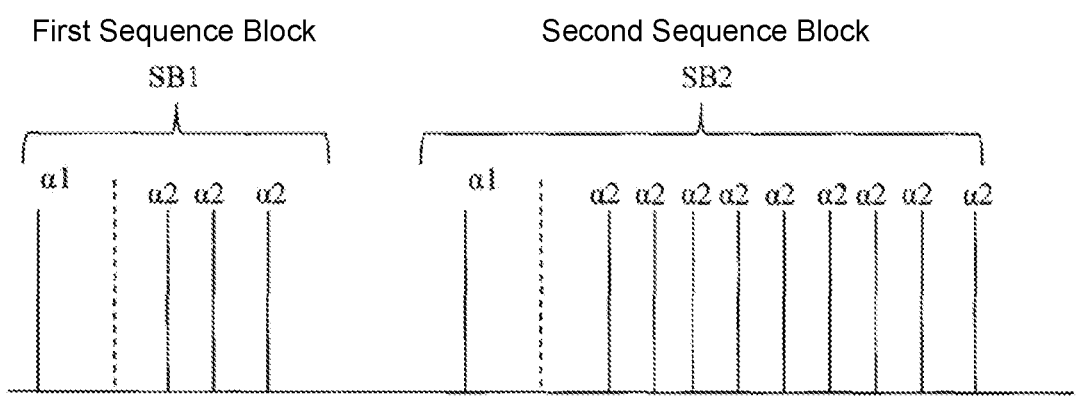
FIG. 4 illustrates an example set of sequence blocks.

FIG. 4 illustrates another example set of sequence blocks. In FIG. 4, a first sequence block SB1 has a first alpha pulse $\alpha 1$ and a series of identical $\alpha 2$ pulses. In FIG. 4, a second sequence block SB2 has the same first alpha pulse $\alpha 1$ and a different series of identical $\alpha 2$ pulses. The phase may be the same for the $\alpha 2$ pulses. Thus, in this example, the only difference between members of the set of sequence blocks is the number of $\alpha 2$ pulses. One skilled in the art will appreciate that other sets of sequence blocks may be employed.

Example apparatus and methods may design a pulse sequence for an acquisition scheme that samples data in the most efficient method possible. In different embodiments, multi-echo radial or spiral trajectories may be employed since aliasing artifacts from under-sampling may be more incoherent. In one embodiment, a 3D trajectory may be employed. Uniform sampling density and non-uniform sampling density may be employed with multi-echo radial or spiral trajectories. Non-uniform density sampling may be controlled to sample more heavily in directions with poor detector coil performance to compensate for that poor detector coil performance.

Multi-echo and multi-spiral trajectories have under-sampling alias artifacts that are more incoherent. The multi-echo and multi-spiral trajectories may be modified as a function of field inhomogeneity. For example, frequency specific RF excitations may be selectively applied to regions based on the homogeneity or inhomogeneity of the region. An inhomogeneity may be fabricated and frequency specific RF excitations may be customized for the multi-echo or multi-spiral trajectories based on the presence, type, strength, or other property of the inhomogeneity.

Figure 1:
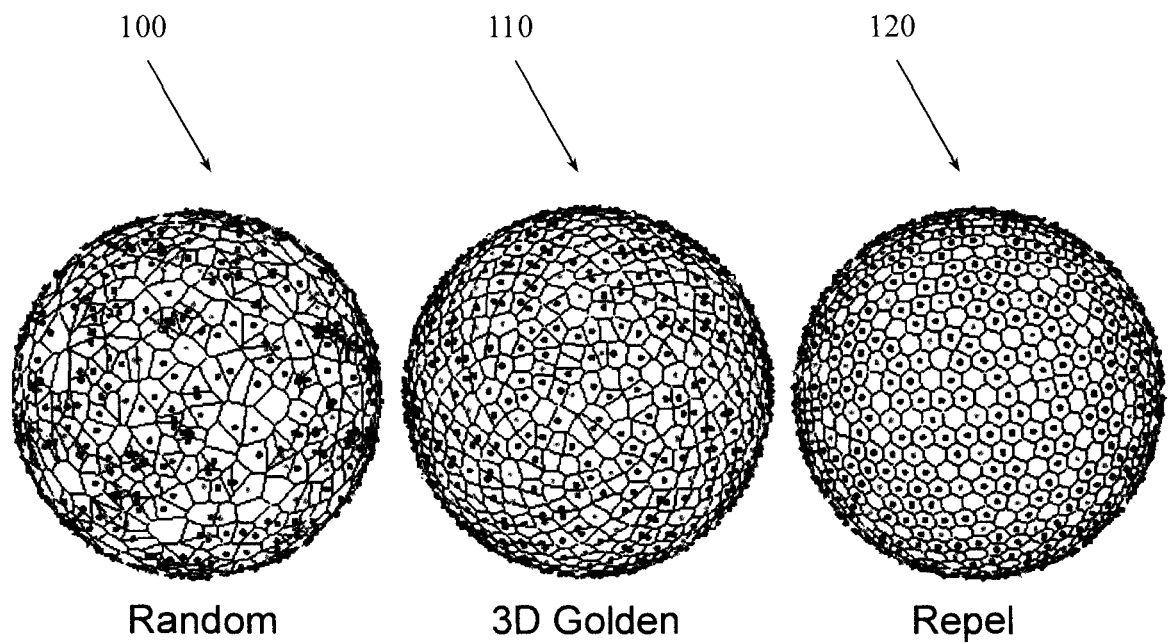
FIG. 1 illustrates projection locations from random, 3D Golden, and Charge Repulsion approaches.

In one embodiment, a sampling pattern may be determined using simulations of electric charge distributions on a surface of a sphere. The charge and sphere sampling approach may be designed to find uniform distributions. See, for example, Lee, G. R., Seiberlich, N., Sunshine, J. L., Carroll, T. J., Griswold, M. A. (2013) Rapid time-resolved magnetic resonance angiography via a multiecho radial trajectory and GraDes reconstruction, Magnetic Resonance in Medicine, 69(2): 346-59. FIG. 1 illustrates projection locations for random 100, 3D Golden 110, and Charge Repulsion 120 models. Charge Repulsion 120 has the most evenly distributed projections.

MRF experiments may generally be performed in a relatively homogeneous magnetic field. However, MRF facilitates significant improvements when combining static or near-static inhomogeneities with frequency selective RF pulses. Consider a conventional gradient oriented in the left-right direction. Example apparatus and methods may excite a frequency band corresponding to the left half of the plane different than a frequency band corresponding to the right half of the plane. When separate excitation patterns are used, signal from the two halves may be uncorrelated and may therefore be separated through pattern recognition. While two separate excitation patterns are described being used for the two halves, a greater number of excitation patterns may be used for a greater number of different regions having different magnetization due to existing or created inhomogeneities.

Figure 2:
FIG. 2 illustrates IR-bSSFP phantom experiment results for homogeneous and inhomogeneous magnetic fields.

Field inhomogeneities may be exploited to enhance the spatial separation of an MRF signal. Conventionally, field inhomogeneities may distort an MR image and thus attempts have been made to correct for and remove the field inhomogeneities. Example apparatus and methods may use field inhomogeneities as spatial information to un-alias pixels, which may in turn facilitate reducing acquisition time. Acquisition time may be reduced because field inhomogeneities yield different signal time courses in two given pixels even if all other tissue properties are identical, which facilitates disambiguating or unaliasing signal from the two given pixels. FIG. 2 illustrates IR-bSSFP phantom experiment results for homogenous 200 and dynamically inhomogeneous 220 magnetic fields. The dynamically inhomogeneous magnetic field yields a more ideal cross-correlation matrix 230 and allows for more independent signal evolutions, which helps to separate pixels compared to the homogeneous magnetic field case.

Example charge on a sphere trajectories may account for static or dynamic inhomogeneities to further decrease scan time. Static inhomogeneities may already exist in a magnetic field. Dynamic inhomogeneities may be added to or manipulated in a magnetic field. The dynamic inhomogeneities may be produced, for example, by gradients, by quadrapolar fields, by shim coils, or in other ways. In one embodiment, an inhomogeneity may be differentially varied in different numbers or types of encoding axes during acquisition. The inhomogeneity may also be varied in strength or direction.

Consider a very inhomogeneous magnet. One embodiment may separately excite different parts of the magnet. The number of different excitations may by limited by the RF receive bandwidth or cross-correlation between the different excitation areas. This may facilitate performing MRF on lower cost magnets. This may also facilitate producing significantly faster coverage of a given volume per unit of time.

The MRF pulse sequence produces a signal evolution from which multiple MR parameters may be quantified in a single acquisition. In one embodiment, the signal evolution may be described by:

$$SE = \Pi_{i=1}^{NA} \Sigma_{j=1}^{NRF} R_i(\alpha) R_{RFij}(\alpha,\varphi) R(G) E_i(T1,T2,D) M_0 \quad [1]$$

where:
 SE is a signal evolution,
 $N_A$ is a number of sequence blocks,
 $N_{RF}$ is a number of RF pulses in a sequence block,
 $\alpha$ is a flip angle,
 $\varphi$ is a phase angle,
 Ri($\alpha$) is a rotation due to off resonance,
 $R_{RFij}(\alpha,\varphi)$ is a rotation due to RF differences,
 R(G) is a rotation due to a gradient,
 T1 is spin-lattice relaxation,
 T2 is spin-spin relaxation,
 D is diffusion relaxation,
 $E_i$(T1,T2,D) is decay due to relaxation differences, and
 $M_0$ is the default or equilibrium magnetization.

While $E_i$(T1,T2,D) is provided as an example, one skilled in the art will appreciate that in different embodiments, $E_i$(T1,T2,D) may actually be $E_i$(T1,T2,D, . . . ), or $E_i$(T1, T2, . . . ).

In one example, the summation on j could be replaced by a product on j:

$$SE = \Pi_{i=1}^{NA} \pi_{j=1}^{NRF} R_i(\alpha) R_{RFij}(\alpha,\varphi) R(G) E_i(T1,T2,D) M_0 \quad [2]$$

In NMR, MRI, or ESR (electron spin resonance), a Bloch equation is a member of a set of macroscopic equations that are used to calculate the nuclear magnetization $M=(M_x, M_y, M_z)$ as a function of time when relaxation times T1 and T2 are present. These phenomenological equations were introduced by Felix Bloch and may also be referred to as the equations of motion of nuclear magnetization. One skilled in the art will appreciate that in one embodiment Ri($\alpha$), $R_{RFij}$ ($\alpha,\varphi$), and R(G) may be viewed as Bloch equations.

The MRF pulse sequence produces a signal evolution from which multiple MR parameters may be quantified in a single acquisition. In one embodiment, the signal evolution may be described by:

$$S_i = R_i E_i(S_{i-1}) \quad [3]$$

or $$S_i = R_i E_i \sum_{x=1}^{i-1} R_x E_x(S_x) \quad [4]$$

or $$S_i = R_i E_i \prod_{x=1}^{i-1} R_x E_x(S_x) \quad [5]$$

where:
 $S_0$ is the default or equilibrium magnetization,
 $S_i$ is a vector that represents the different components of the magnetization Mx, My, Mz during acquisition block i,
 $R_i$ is the combination of rotational effects that occur during acquisition block i, and
 $E_i$ is the combination of effects that alter the amount of magnetization in the different states for acquisition block i.

The MRF pulse sequence produces a signal evolution from which multiple MR parameters may be quantified in a single acquisition. In one embodiment, the signal evolution may be described by:

$$S_i = \sum_{s=1}^{N_S} R_{s,i} E_{s,i}(S_{s,i-1}) \quad [6]$$

or $$S_i = \sum_{s=1}^{N_S} R_{s,i} E_{s,i} \sum_{x=1}^{i-1} R_{s,x} E_{s,x}(S_{s,x}) \quad [7]$$

or $$S_i = \sum_{s=1}^{N_S} R_{s,i} E_{s,i} \prod_{x=1}^{i-1} R_{s,x} E_{s,x}(S_{s,x}) \quad [8]$$

where:
 $S_0$ is the default or equilibrium magnetization,
 Ns is the number of spins,
 $S_i$ is a vector that represents the different components of the magnetization Mx, My, Mz during acquisition block i,
 $R_{i,s}$ is the sum of rotational effects that occur during acquisition block i for spin s, and
 $E_{i,s}$ is the sum of effects that alter the amount of magnetization in the different states for acquisition block i for spin s.

Some portions of the detailed descriptions that follow are presented in terms of algorithms and symbolic representations of operations on data bits within a memory. These algorithmic descriptions and representations are used by those skilled in the art to convey the substance of their work to others. An algorithm is considered to be a sequence of operations that produce a result. The operations may include creating and manipulating physical quantities that may take the form of electronic values. Creating or manipulating a physical quantity in the form of an electronic value produces a concrete, tangible, useful, real-world result.

It has proven convenient at times, principally for reasons of common usage, to refer to these signals as bits, values, elements, symbols, characters, terms, numbers, and other terms. It should be borne in mind, however, that these and similar terms are to be associated with the appropriate physical quantities and are merely convenient labels applied to these quantities. Unless specifically stated otherwise, it is appreciated that throughout the description, terms including processing, computing, and determining, refer to actions and processes of a computer system, logic, processor, or similar electronic device that manipulates and transforms data represented as physical quantities (e.g., electronic values).

Example methods may be better appreciated with reference to flow diagrams. For simplicity, the illustrated methodologies are shown and described as a series of blocks.

However, the methodologies may not be limited by the order of the blocks because, in some embodiments, the blocks may occur in different orders than shown and described. Moreover, fewer than all the illustrated blocks may be required to implement an example methodology. Blocks may be combined or separated into multiple components. Furthermore, additional or alternative methodologies can employ additional, not illustrated blocks.

Figure 5:
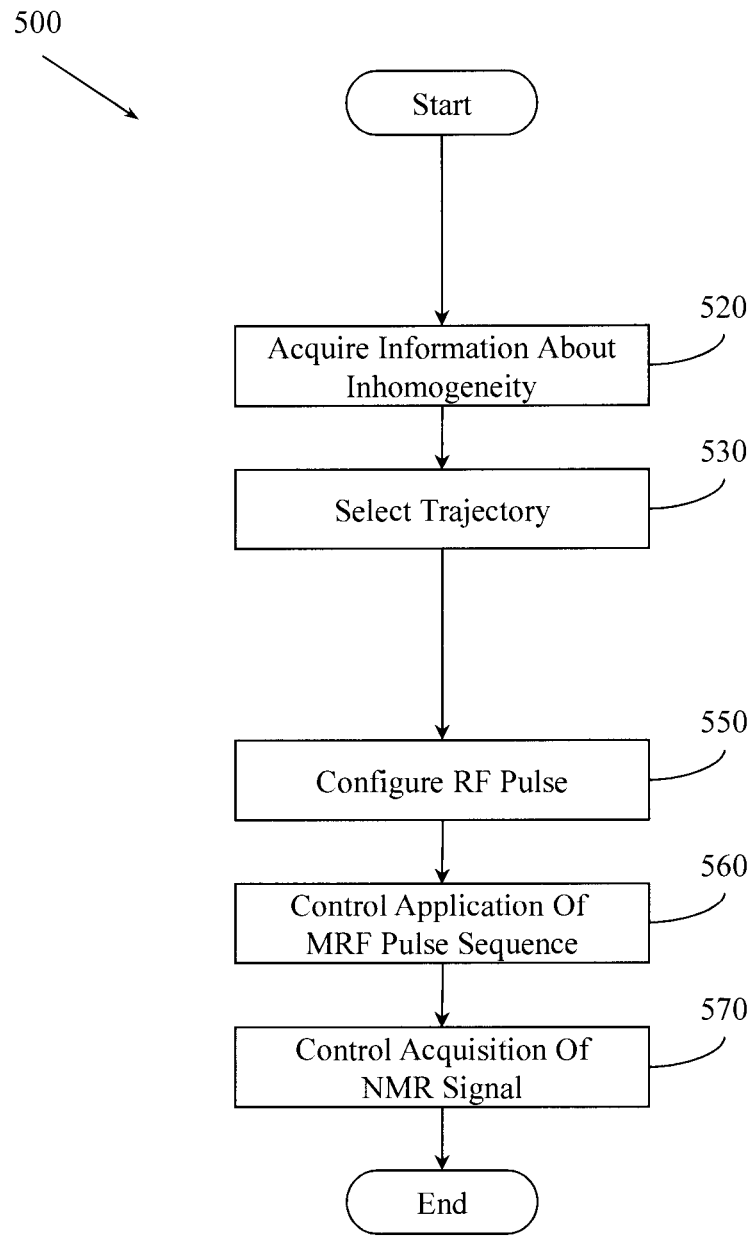
FIG. 5 illustrates an example method for improved MRF.

FIG. 5 illustrates an example method 500. Method 500 involves acquiring information about or creating an inhomogeneity in a magnetic field associated with an MRI apparatus that is going to perform MRF. The inhomogeneity may be fixed or may vary. The inhomogeneity may vary up to each acquisition period during an MRF pulse sequence. The inhomogeneity may be controlled to be less than $2\pi$ per voxel. Once information about the inhomogeneity is known, the MRF may proceed with a regularly scheduled trajectory or with a trajectory that is selected based, at least in part, on the information about the inhomogeneity. Similarly, once information about the inhomogeneity is known, then regularly scheduled acquisition periods or flip angles may be employed or acquisition periods or flip angles can be optimized based, at least in part, on the inhomogeneity. Additionally, once information about the inhomogeneity is available, then the frequency or timing of RF pulses applied during the MRF pulse sequence can be selectively manipulated based, at least in part, on the inhomogeneity.

Method 500 includes, at 520, acquiring information about an inhomogeneity in a magnetic field associated with an MRI apparatus that will apply an MRF pulse sequence to an object located in the magnetic field. Acquiring information about the inhomogeneity may include characterizing the inhomogeneity with respect to one or more attributes. The attributes may include, for example, the size, shape, or location of the inhomogeneity. The attribute may also include, for example, an axis or axes along which the inhomogeneity is aligned.

Method 500 may also include, at 530, selecting an acquisition trajectory for an acquisition of NMR signals that will be generated by the object in response to the MRF pulse sequence. A regularly scheduled trajectory may be employed or the acquisition trajectory may be selected based, at least in part, on the existence of or on an attribute or property of the inhomogeneity. For example, an inhomogeneity with a first property may cause a first trajectory to be selected while an inhomogeneity with a second property may cause a second trajectory to be selected. The acquisition trajectory may be, for example, a multi-echo radial trajectory or a spiral or multi-spiral trajectory. The acquisition trajectory may be a uniform trajectory or a non-uniform trajectory. In one embodiment, the uniform trajectory is based, at least in part, on a model of charge distribution on a sphere. The model may be, for example, a Golden Sphere model or a Charge Repulsion model. When the trajectory is a non-uniform trajectory, the amount of sampling performed in an area by the non-uniform trajectory may be inversely proportional to the detector coil performance in the area. The acquisition trajectory may be a 3D trajectory.

Method 500 may also include, at 550, selecting or configuring a frequency selective RF pulse to include in the MRF pulse sequence. A regularly scheduled RF pulse may be employed or the frequency selective RF pulse may be based, at least in part, on the inhomogeneity or the acquisition trajectory. For example, a first type of inhomogeneity and a first type of acquisition trajectory may cause a first type of frequency selective RF pulse to be selected while a second type of inhomogeneity and a second type of acquisition trajectory may cause a second type of frequency selective RF pulse to be selected. The frequency selective RF pulse may be configured with respect to, for example, frequency, flip angle, repetition time, or other attributes. Thus, both frequency and timing of RF pulses may be manipulated based, at least in part, on the in homogeneity.

Method 500 may also include, at 560, controlling the MRI apparatus to apply the MRF pulse sequence with the frequency selective RF pulse to the object. Applying the MRF pulse sequence may include controlling gradients and RF pulses. Method 500 may also include, at 570, controlling the MRI apparatus to acquire the resulting NMR signals according to the acquisition trajectory. The object may then be characterized using MRF on the resulting NMR signals.

Figure 6:
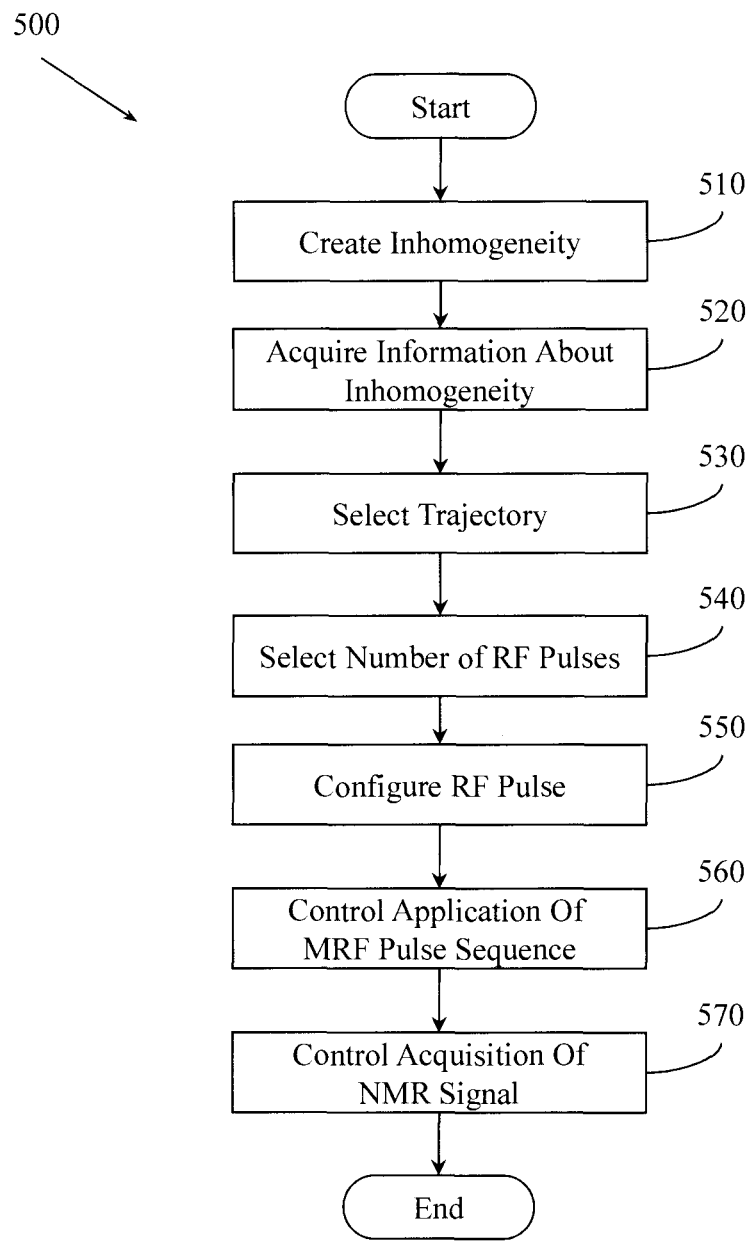
FIG. 6 illustrates an example method for improved MRF.

FIG. 6 illustrates another embodiment of method 500. This embodiment also includes, at 510, creating the inhomogeneity. Creating the inhomogeneity may include varying a size, shape, direction, or number of axes associated with the inhomogeneity. The properties of the inhomogeneity may be varied by controlling a field gradient produced by the MRI apparatus, by controlling a quadrapolar field produced by the MRI apparatus, by controlling a shim coil available to the MRI apparatus, or in other ways. While a single inhomogeneity is described, two or more inhomogeneities may be produced. The different inhomogeneities may have different properties (e.g., size, shape, location).

This embodiment of method 500 may also include, at 540, selecting a number of frequency selective RF pulses to include in the MRF pulse sequence. The number of frequency selective RF pulses may be determined by, for example, the receive bandwidth of the MRI apparatus, by the cross correlation between different excitation areas associated with the RF pulses, or in other ways. For example, the number of frequency selective RF pulses may vary directly with the receive bandwidth of the MRI apparatus. The timing for the frequency selective RF pulses may also be controlled based, at least in part, on the inhomogeneity.

Figure 7:
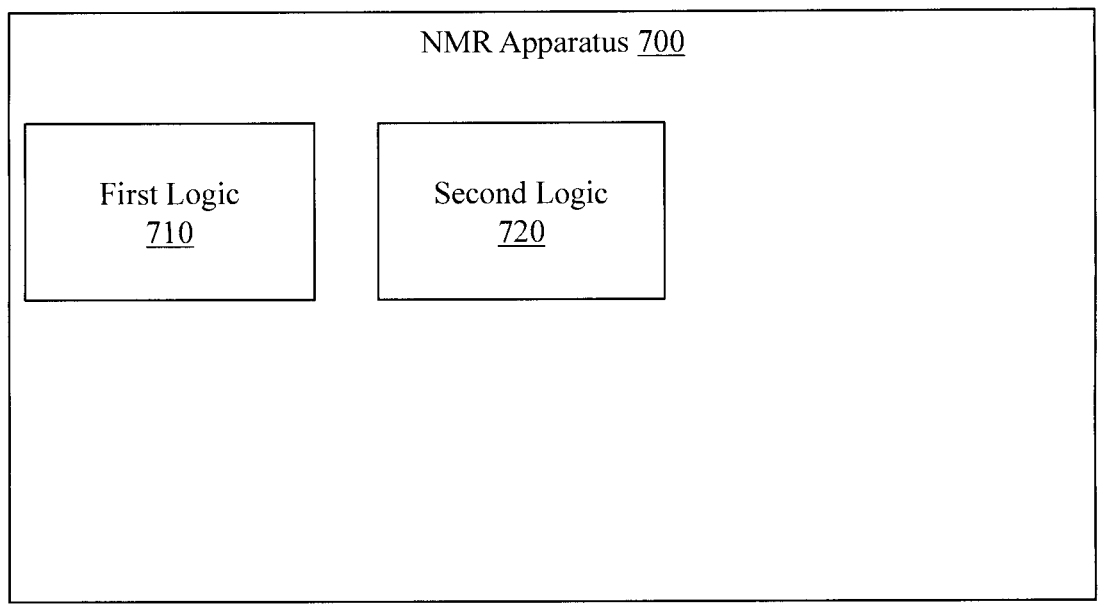
FIG. 7 illustrates an example apparatus that performs improved MRF.

FIG. 7 illustrates an example NMR apparatus 700. NMR apparatus 700 includes a first logic 710 that selects an acquisition trajectory for acquiring NMR signals generated by an object in response to an MRF pulse sequence applied to the object by the NMR apparatus 700. NMR apparatus 700 may have different types of acquisition trajectories available to apply. The acquisition trajectories may be based on a charge distribution on a sphere model. For example, the model may be a Golden Sphere model or a Charge Repulsion model. The acquisition trajectory may also be a multi-echo trajectory. For example, the trajectory may be a multi-echo radial trajectory or a spiral or multi-spiral trajectory. Which acquisition trajectory is selected may be based on, for example, a property of an inhomogeneity in the magnetic field produced by apparatus 700. Whether the acquisition trajectory is uniform or non-uniform may also be based, for example, on a property of an inhomogeneity in the magnetic field produced by apparatus 700. The acquisition trajectory may be a 3D acquisition trajectory.

Apparatus 700 also includes second logic 720 that controls the MRI apparatus 700 to apply the MRF pulse sequence to the object. Controlling the MRI apparatus 700 to apply the MRF pulse sequence may include controlling gradients, RF pulses, and other actions.

In one embodiment, the first logic 710 controls the pulse sequence to produce a signal evolution from which two or more MR parameters may be quantified in a single acquisition. In different embodiments, the signal evolution may be described by any of equations 1-8.

Figure 8:
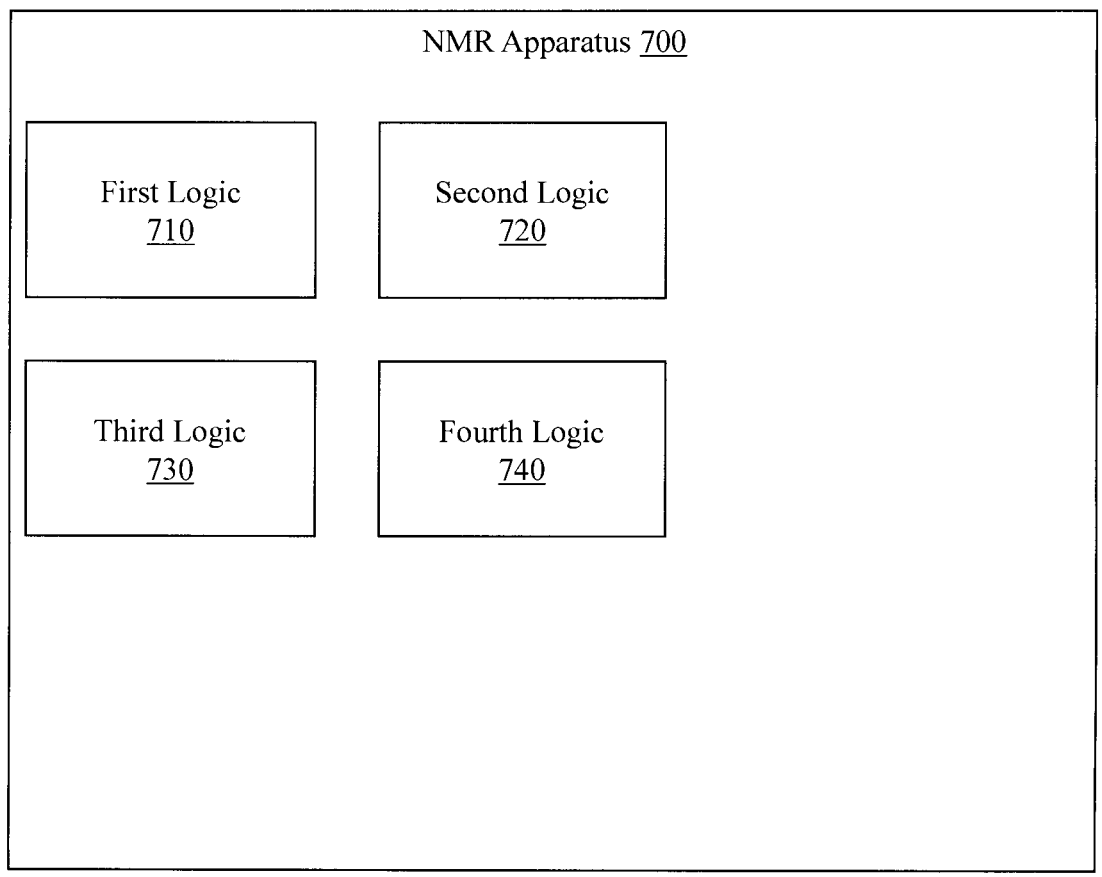
FIG. 8 illustrates an example apparatus that performs improved MRF.

FIG. 8 illustrates another embodiment of apparatus 700. This embodiment of apparatus 700 also includes a third logic 730 that acquires information about an inhomogeneity in a magnetic field produced by the MRI apparatus 700. The third logic 730 manipulates a frequency selective RF pulse in the MRF pulse sequence based on a property of the inhomogeneity. For example, the frequency, timing, number, flip angle, repetition time, or other attribute of the frequency selective RF pulse may be manipulated based on the location, size, orientation, or other property of the inhomogeneity.

This embodiment of apparatus 700 also includes a fourth logic 740 that creates a fabricated inhomogeneity in the magnetic field. Creating the fabricated inhomogeneity may include controlling a field gradient produced by the NMR apparatus 700, controlling a quadrapolar field produced by the NMR apparatus 700, controlling a shim coil that is available to the NMR apparatus 700, or in other ways. While a single inhomogeneity is described, two or more inhomogeneities may be produced. The different inhomogeneities may have different properties (e.g., size, shape, location).

Figure 9:
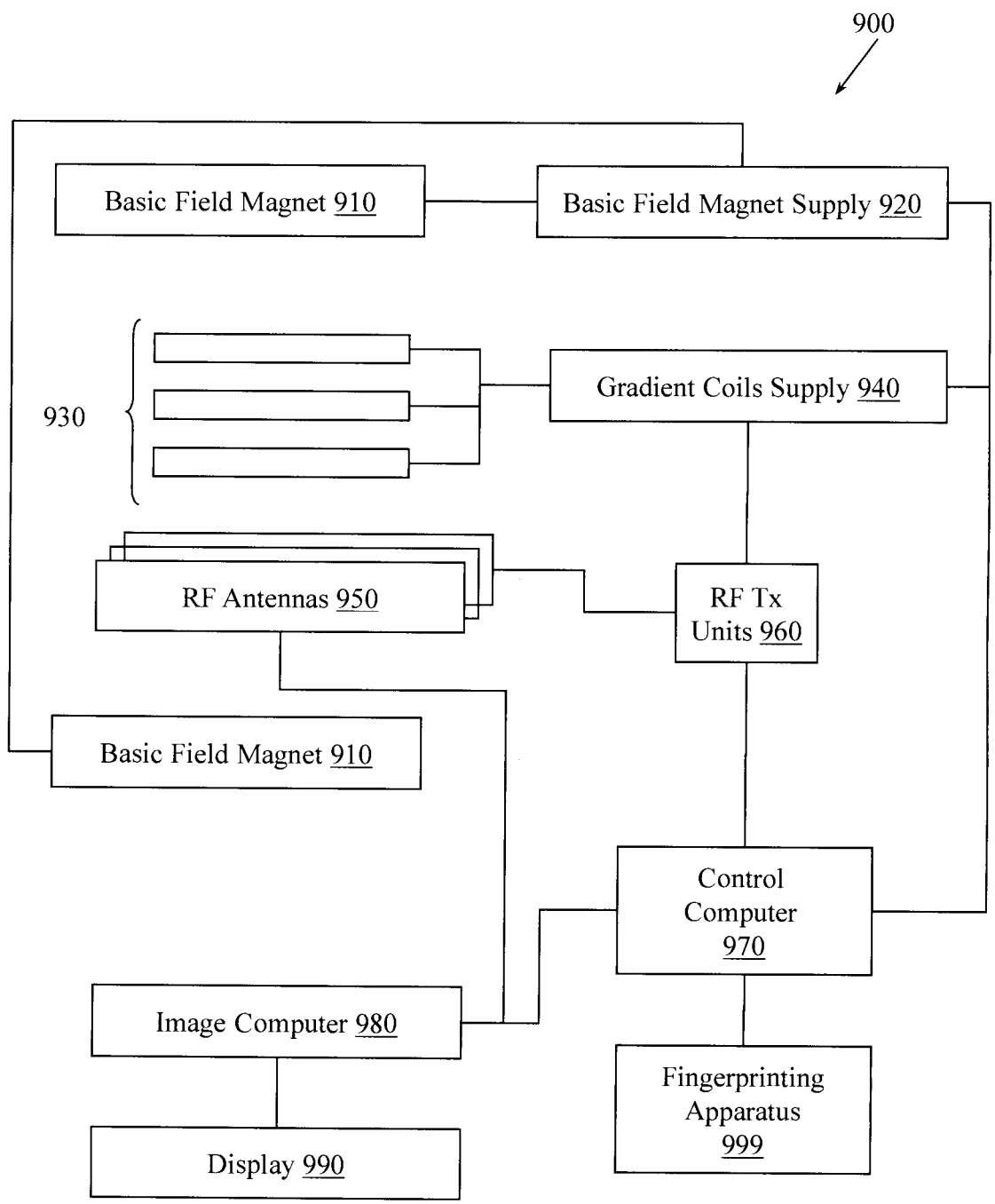
FIG. 9 illustrates an example MRI apparatus that performs improved MRF.

FIG. 9 illustrates an example MRI apparatus 900 that has a fingerprinting apparatus 999 to facilitate MRI fingerprinting. The fingerprinting apparatus 999 may have elements of example apparatus described herein and/or may perform example methods described herein. For example, the fingerprinting apparatus 999 may have circuits or logics that improve MRF by using frequency selective RF pulses in an MRF pulse sequence that capitalizes on spatial inhomogeneities in a magnetic field produced by apparatus 900.

In one embodiment, fingerprinting apparatus 999 may perform a method that includes performing 3D MRF with optimized spatial encoding and parallel imaging in an inhomogeneous magnetic field. In one embodiment, the spatial encoding and parallel imaging use spatial information associated with an inhomogeneity in the inhomogeneous magnetic field to unalias pixels and to enhance spatial separation of an MRF signal. The parallel imaging may involve a multi-echo radial trajectory or spiral trajectory that acquires data according to sampling schemes based on a model of charge distribution on a sphere. In one embodiment, the 3D MRF includes an MRF pulse sequence that includes a frequency selective RF pulse that is determined, at least in part, by the field inhomogeneity.

The apparatus 900 includes a basic field magnet(s) 910 and a basic field magnet supply 920. Ideally, the basic field magnets 910 would produce a uniform $B_0$ field. However, in practice, the $B_0$ field may not be uniform, and may vary over an object being imaged by the MRI apparatus 900. MRI apparatus 900 may include gradient coils 930 configured to emit gradient magnetic fields like $G_S$, $G_P$ and $G_R$. The gradient coils 930 may be controlled, at least in part, by a gradient coils supply 940. In some examples, the timing, strength, and orientation of the gradient magnetic fields may be controlled, and thus selectively adapted, during an MRI procedure.

MRI apparatus 900 may include a set of RF antennas 950 that generate RF pulses and receive resulting NMR signals from an object to which the RF pulses are directed. In some examples, how the pulses are generated and how the resulting MR signals are received may be controlled and thus may be selectively adapted during an MR procedure. Separate RF transmission and reception coils can be employed. The RF antennas 950 may be controlled, at least in part, by a set of RF transmission units 960. An RF transmission unit 960 may provide a signal to an RF antenna 950.

The gradient coils supply 940 and the RF transmission units 960 may be controlled, at least in part, by a control computer 970. In one example, the control computer 970 may be programmed to control an NMR device as described herein. Conventionally, the MR signals received from the RF antennas 950 can be employed to generate an image and thus may be subject to a transformation process like a two dimensional Fast Fourier Transform (FFT) that generates pixilated image data. The transformation can be performed by an image computer 980 or other similar processing device. The image data may then be shown on a display 990.

However, fingerprinting apparatus 999 facilitates not having to do conventional reconstruction of an image from MR signals received from the RF antennas 950. Thus the RF energy applied to an object by apparatus 900 need not be constrained to produce signals with substantially constant amplitudes or phases. Instead, fingerprinting apparatus 999 facilitates matching received signals to known signals for which a reconstruction, relaxation parameter, or other information is already available. This facilitates producing a quantitative result.

While FIG. 9 illustrates an example MRI apparatus 900 that includes various components connected in various ways, it is to be appreciated that other MRI apparatus may include other components connected in other ways.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

In one embodiment, the functionality associated with a logic may be performed, at least in part, by hardware logic components including, but not limited to, field-programmable gate arrays (FPGAs), application specific integrated circuits (ASICs), application specific standard products (AS-SPs), system on a chip systems (SOCs), or complex programmable logic devices (CPLDs).

"User", as used herein, includes but is not limited to one or more persons, software, computers or other devices, or combinations of these.

To the extent that the term "includes" or "including" is employed in the detailed description or the claims, it is inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

What is claimed is:

1. A method, comprising:
    acquiring information concerning a $B_0$ inhomogeneity in a magnetic field associated with a magnetic resonance imaging (MRI) apparatus, where the MRI apparatus will apply a magnetic resonance fingerprinting (MRF) pulse sequence to an object located in the magnetic field;
    selecting an acquisition trajectory based, at least in part, on the inhomogeneity for an acquisition of nuclear magnetic resonance (NMR) signals that will be generated by the object in response to the MRF pulse sequence;
    selecting a frequency selective radio frequency (RF) pulse to include in the MRF pulse sequence;
    controlling the MRI apparatus to apply the MRF pulse sequence including the frequency selective RF pulse to the object, and
    controlling the MRI apparatus to acquire the resulting NMR signals according to the acquisition trajectory.

2. The method of claim 1, where the RF pulse is selected based, at least in part, on the inhomogeneity or the acquisition trajectory.

3. The method of claim 2, comprising creating the inhomogeneity.

4. The method of claim 3, where creating the inhomogeneity includes varying a size, shape, direction, or number of axes associated with the inhomogeneity.

5. The method of claim 3, where creating the inhomogeneity includes controlling a field gradient produced by the MRI apparatus, a quadrapolar field produced by the MRI apparatus, or a shim coil manipulated by the MRI apparatus.

6. The method of claim 3, comprising controlling the inhomogeneity to be constant throughout the MRF pulse sequence.

7. The method of claim 3, comprising controlling the inhomogeneity to vary during the MRF pulse sequence.

8. The method of claim 3, comprising controlling the inhomogeneity to vary per acquisition period of the MRF pulse sequence.

9. The method of claim 3, comprising controlling the inhomogeneity to be less than $2\pi$ per voxel.

10. The method of claim 4, comprising selecting a timing for a parameter of the MRF pulse sequence.

11. The method of claim 10, where the timing is selected based, at least in part, on the inhomogeneity.

12. The method of claim 4, comprising selecting a flip angle for the MRF pulse sequence.

13. The method of claim 12, where the flip angle is selected based, at least in part, on the inhomogeneity.

14. The method of claim 1, where the acquisition trajectory is a multi-echo radial trajectory or a spiral trajectory.

15. The method of claim 1, where the acquisition trajectory is a uniform trajectory.

16. The method of claim 15, where the uniform trajectory is based, at least in part, on a model of charge distribution on a sphere.

17. The method of claim 16, where the model is a Golden Sphere model or a Charge Repulsion model.

18. The method of claim 14, where the trajectory is a non-uniform trajectory.

19. The method of claim 18, where the amount of sampling performed in an area by the non-uniform trajectory is inversely proportional to the detector coil performance in the area.

20. The method of claim 1, comprising selecting a number N of frequency selective RF pulses to include in the MRF pulse sequence, where N is determined by the receive bandwidth of the MRI apparatus, N being an integer.

21. The method of claim 1, comprising selecting a number N of frequency selective RF pulses to include in the MRF pulse sequence, where N is determined by the cross correlation between different excitation areas associated with the N RF pulses, N being an integer.

22. The method of claim 1, where the pulse sequence is designed to produce a signal evolution from which two or more MR parameters may be quantified in a single acquisition, where the signal evolution is described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T1, T2, D) M_0$$

or $$SE = \sum_{s=1}^{N_S} \prod_{i=1}^{N_A} \prod_{j=1}^{N_{RF}} R_i(\alpha) R_{RF_{ij}}(\alpha, \phi) R(G) E_i(T1, T2, D) M_0$$

where:
SE is a signal evolution,
$N_S$ is a number of spins,
$N_A$ is a number of sequence blocks,
$N_{RF}$ is a number of RF pulses in a sequence block,
α is a flip angle,
ϕ is a phase angle,
Ri(α) is a rotation due to off resonance,
RRFij(α,ϕ) is a rotation due to RF differences,
R(G) is a rotation due to a gradient,
T1 is spin-lattice relaxation,
T2 is spin-spin relaxation,
D is diffusion relaxation,
$E_i(T1,T2,D)$ is decay due to relaxation differences, and
$M_0$ is the default or equilibrium magnetization.

23. The method of claim 1, where the pulse sequence is designed to produce a signal evolution from which two or more MR parameters may be quantified in a single acquisition, where the signal evolution is described by:

$$S_i = R_i E_i(S_{i-1}) \text{ or}$$

$$S_i = R_i E_i \sum_{x=1}^{i-1} R_x E_x(S_x) \text{ or}$$

$$S_i = R_i E_i \prod_{x=1}^{i-1} R_x E_x(S_x)$$

where:
$S_0$ is the default or equilibrium magnetization,
$S_i$ is a vector that represents the different components of the magnetization Mx, My, Mz during acquisition block i,
$R_i$ is the combination of rotational effects that occur during acquisition block i, and
$E_i$ is the combination of effects that alter the amount of magnetization in the different states for acquisition block i.

24. The method of claim 1, where the pulse sequence is designed to produce a signal evolution from which two or more multiple MR parameters may be quantified in a single acquisition, where the signal evolution is described by:

$$S_i = \sum_{s=1}^{N_S} R_{s,i} E_{s,i}(S_{s,i-1}) \text{ or}$$

$$S_i = \sum_{s=1}^{N_S} R_{s,i} E_{s,i} \sum_{x=1}^{i-1} R_{s,x} E_{s,x}(S_{s,x}) \text{ or}$$

$$S_i = \sum_{s=1}^{N_S} R_{s,i} E_{s,i} \prod_{x=1}^{i-1} R_{s,x} E_{s,x}(S_{s,x})$$

where:
$S_0$ is the default or equilibrium magnetization,
Ns is the number of spins,
$S_i$ is a vector that represents the different components of the magnetization Mx, My, Mz during acquisition block i,
$R_{i,s}$ is the sum of rotational effects that occur during acquisition block i for spin s, and
$E_{i,s}$ is the sum of effects that alter the amount of magnetization in the different states for acquisition block i for spins.

25. A nuclear magnetic resonance (NMR) apparatus, comprising:
a computer system configured to select an acquisition trajectory for acquiring NMR signals generated by an object in response to a magnetic resonance fingerprinting (MRF) pulse sequence applied to the object by the NMR apparatus, where the acquisition trajectory is selected based on a charge distribution on a sphere model, and where the acquisition trajectory is a multi-echo radial trajectory or a spiral trajectory, and
wherein the computer system is configured to control the MRI apparatus to apply the MRF pulse sequence to the object.

26. The NMR apparatus of claim 25, wherein the computer system acquires information about an inhomogeneity in a magnetic field produced by the MRI apparatus and that manipulates a frequency selective radio frequency (RF) pulse in the MRF pulse sequence based on a property of the inhomogeneity.

27. The NMR apparatus of claim 26, wherein the computer system selects the acquisition trajectory based, at least in part, on the inhomogeneity.

28. The NMR apparatus of claim 26, wherein the computer system controls the acquisition trajectory to be non-uniform based, at least in part, on the inhomogeneity.

29. The NMR apparatus of claim 26, wherein the computer system creates a fabricated inhomogeneity in the magnetic field.

30. The NMR apparatus of claim 29, wherein the computer system selects the acquisition trajectory based, at least in part, on the fabricated inhomogeneity.

31. The NMR apparatus of claim 30, wherein the computer system controls the acquisition trajectory to be non-uniform based, at least in part, on the inhomogeneity.

32. The NMR apparatus of claim 31, wherein the computer system manipulates the frequency selective RF pulse based, at least in part, on a property of the fabricated inhomogeneity.

33. The NMR apparatus of claim 26, wherein the computer system controls the pulse sequence to produce a signal evolution from which two or more MR parameters may be quantified in a single acquisition, where the signal evolution is described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T1, T2, D) M_0$$

or $$SE = \sum_{s=1}^{N_S} \prod_{i=1}^{N_A} \prod_{j=1}^{N_{RF}} R_i(\alpha) R_{RF_{ij}}(\alpha, \phi) R(G) E_i(T1, T2, D) M_0$$

where:
SE is a signal evolution,
$N_S$ is a number of spins,
$N_A$ is a number of sequence blocks,
$N_{RF}$ is a number of RF pulses in a sequence block,
$\alpha$ is a flip angle,
$\phi$ is a phase angle,
$Ri(\alpha)$ is a rotation due to off resonance,
$R_{RFit}(\alpha,\phi)$ is a rotation due to RF differences,
$R(G)$ is a rotation due to a gradient,
T1 is spin-lattice relaxation,
T2 is spin-spin relaxation,
D is diffusion relaxation,
$E_i(T1,T2,D)$ is decay due to relaxation differences, and
Mo is the default or equilibrium magnetization.

34. The NMR apparatus of claim 26, wherein the computer system controls the pulse sequence to produce a signal evolution from which two or more MR parameters may be quantified in a single acquisition, where the signal evolution is described by:

$$S_i = R_i E_i(S_{i-1}) \text{ or}$$

$$S_i = R_i E_i \sum_{x=1}^{i-1} R_x E_x(S_x) \text{ or}$$

$$S_i = R_i E_i \prod_{x=1}^{i-1} R_x E_x(S_x)$$

where:

$S_0$ is the default or equilibrium magnetization, $S_i$ is a vector that represents the different components of the magnetization Mx, My, Mz during acquisition block i, $R_i$ is the combination of rotational effects that occur during acquisition block i, and $E_i$ is the combination of effects that alter the amount of magnetization in the different states for acquisition block i.

35. The NMR apparatus of claim 26, wherein the computer system controls the pulse sequence to produce a signal evolution from which two or more MR parameters may be quantified in a single acquisition, where the signal evolution is described by:

$$S_i = \sum_{s=1}^{N_s} R_{s,i} R_{s,i}(S_{s,i-1}) \text{ or}$$

$$S_i = \sum_{s=1}^{N_s} R_{s,i} E_{s,i} \sum_{x=1}^{i-1} R_{s,x} E_{s,x}(S_{s,x}) \text{ or}$$

$$S_i = \sum_{s=1}^{N_s} R_{s,i} E_{s,i} \prod_{x=1}^{i-1} R_{s,x} E_{s,x}(S_{s,x})$$

where:

$S_0$ is the default or equilibrium magnetization,

Ns is the number of spins, $S_i$ is a vector that represents the different components of the magnetization Mx, My, Mz during acquisition block i, $R_{i,s}$ is the sum of rotational effects that occur during acquisition block i for spin s, and $E_{i,s}$ is the sum of effects that alter the amount of magnetization in the different states for acquisition block i for spin s.

36. A method for improved magnetic resonance fingerprinting (MRF), comprising:
performing two dimensional or three dimensional (3D) MRF with a magnetic resonance imaging (MRI) system with a computer system configured with optimized spatial encoding and parallel imaging in an inhomogeneous magnetic field, where the spatial encoding and parallel imaging use spatial information associated with an inhomogeneity in the inhomogeneous magnetic field to unalias pixels and to enhance spatial separation of an MRF signal received from an object in the inhomogeneous magnetic field, and where the parallel imaging involves a multi-echo radial trajectory or spiral trajectory that acquires data from the object according to sampling schemes based on a model of charge distribution on a sphere.

37. The method of 36, where the MRF includes an MRF pulse sequence that includes a frequency selective RF pulse that is determined, at least in part, by the field inhomogeneity.

38. A method, comprising:
acquiring information concerning a $B_0$ inhomogeneity in a magnetic field associated with a magnetic resonance imaging (MRI) apparatus, where the MRI apparatus will apply a magnetic resonance fingerprinting (MRF) pulse sequence to an object located in the magnetic field;

selecting an acquisition trajectory for an acquisition of nuclear magnetic resonance (NMR) signals that will be generated by the object in response to the MRF pulse sequence, where the acquisition trajectory is a uniform trajectory;

selecting a frequency selective radio frequency (RF) pulse to include in the MRF pulse sequence;

controlling the MRI apparatus to apply the MRF pulse sequence including the frequency selective RF pulse to the object, and controlling the MRI apparatus to acquire the resulting NMR signals according to the acquisition trajectory.

39. The method of claim 38, where the acquisition trajectory is selected based, at least in part, on the inhomogeneity.

40. The method of claim 39, where the RF pulse is selected based, at least in part, on the inhomogeneity or the acquisition trajectory.

41. The method of claim 40, comprising creating the inhomogeneity by at least one of:
varying a size, shape, direction, or number of axes associated with the inhomogeneity;
controlling a field gradient produced by the MRI apparatus, a quadrapolar field produced by the MRI apparatus, or a shim coil manipulated by the MRI apparatus;
controlling the inhomogeneity to be constant throughout the MRF pulse sequence;
controlling the inhomogeneity to vary during the MRF pulse sequence; or
controlling the inhomogeneity to be less than $2\pi$ per voxel.

42. The method of claim 38, comprising selecting a timing for a parameter of the MRF pulse sequence at least in part based on the inhomogeneity.

43. The method of claim 38, further comprising selecting a flip angle for the MRF pulse sequence based, at least in part, on the inhomogeneity.

44. The method of claim 38, where the acquisition trajectory is a multi-echo radial trajectory or a spiral trajectory.

45. The method of claim 38, where the uniform trajectory is based, at least in part, on a model of charge distribution on a sphere.

46. The method of claim 45, where the model is a Golden Sphere model or a Charge Repulsion model.

47. The method of claim 38, comprising selecting a number N of frequency selective RF pulses to include in the MRF pulse sequence, where N is determined by the receive bandwidth of the MRI apparatus, N being an integer.

48. The method of claim 38, comprising selecting a number N of frequency selective RF pulses to include in the MRF pulse sequence, where N is determined by the cross correlation between different excitation areas associated with the N RF pulses, N being an integer.

49. The method of claim 38, where the pulse sequence is designed to produce a signal evolution from which two or more MR parameters may be quantified in a single acquisition, where the signal evolution is described by:

$$SE = \sum_{s=1}^{N_s} \prod_{i=1}^{N_A} \sum_{j=1}^{N_{RF}} R_i(\alpha) R_{RF_{ij}}(\alpha, \phi) R(G) E_i(T1, T2, D) M_0$$

or

-continued $$SE = \sum_{s=1}^{N_S} \prod_{i=1}^{N_A} \prod_{j=1}^{N_{RF}} R_i(\alpha) R_{RF_{ij}}(\alpha, \phi) R(G) E_i(T1, T2, D) M_0$$

where:
SE is a signal evolution,
$N_S$ is a number of spins,
$N_A$ is a number of sequence blocks,
$N_{RF}$ is a number of RF pulses in a sequence block,
α is a flip angle,
ϕ is a phase angle,
Ri(α) is a rotation due to off resonance,
RRFij(α,ϕ) is a rotation due to RF differences,
R(G) is a rotation due to a gradient,
T1 is spin-lattice relaxation,
T2 is spin-spin relaxation,
D is diffusion relaxation,
$E_i$(T1,T2,D) is decay due to relaxation differences, and
$M_0$ is the default or equilibrium magnetization.

50. The method of claim 38, where the pulse sequence is designed to produce a signal evolution from which two or more MR parameters may be quantified in a single acquisition, where the signal evolution is described by:

$$S_i = R_i E_i (S_{i-1}) \text{ or}$$

$$S_i = R_i E_i \sum_{x=1}^{i-1} R_x E_x (S_x) \text{ or}$$

$$S_i = R_i E_i \prod_{x=1}^{i-1} R_x E_x (S_x)$$

where:
$S_0$ is the default or equilibrium magnetization,
$S_i$ is a vector that represents the different components of the magnetization Mx, My, Mz during acquisition block i,
$R_i$ is the combination of rotational effects that occur during acquisition block i, and
$E_i$ is the combination of effects that alter the amount of magnetization in the different states for acquisition block i.

51. The method of claim 38, where the pulse sequence is designed to produce a signal evolution from which two or more multiple MR parameters may be quantified in a single acquisition, where the signal evolution is described by:

$$S_i = \sum_{s=1}^{N_s} R_{s,i} R_{s,i} (S_{s,i-1}) \text{ or}$$

$$S_i = \sum_{s=1}^{N_s} R_{s,i} E_{s,i} \sum_{x=1}^{i-1} R_{s,x} E_{s,x} (S_{s,x}) \text{ or}$$

$$S_i = \sum_{s=1}^{N_s} R_{s,i} E_{s,i} \prod_{x=1}^{i-1} R_{s,x} E_{s,x} (S_{s,x})$$

where:
$S_0$ is the default or equilibrium magnetization,
Ns is the number of spins,
$S_i$ is a vector that represents the different components of the magnetization Mx, My, Mz during acquisition block i,
$R_{i,s}$ is the sum of rotational effects that occur during acquisition block i for spin s, and
$E_{i,s}$ is the sum of effects that alter the amount of magnetization in the different states for acquisition block i for spin s.

\* \* \* \* \*